US010125352B2

(12) United States Patent
Fenard

(10) Patent No.: US 10,125,352 B2
(45) Date of Patent: Nov. 13, 2018

(54) METHOD FOR PRODUCING ENVELOPED VIRUSES

(71) Applicant: GENETHON, Evry (FR)

(72) Inventor: David Fenard, Mennecy (FR)

(73) Assignee: GENETHON, Evry (FR)

( * ) Notice: Subject to any disclaimer, the term of this patent is extended or adjusted under 35 U.S.C. 154(b) by 0 days.

(21) Appl. No.: 15/022,049

(22) PCT Filed: Sep. 12, 2014

(86) PCT No.: PCT/FR2014/052279
§ 371 (c)(1),
(2) Date: Mar. 15, 2016

(87) PCT Pub. No.: WO2015/036713
PCT Pub. Date: Mar. 19, 2015

(65) Prior Publication Data
US 2016/0230147 A1    Aug. 11, 2016

(30) Foreign Application Priority Data
Sep. 16, 2013   (FR) ..................... 13 58909

(51) Int. Cl.
| | | |
|---|---|---|
| A61K 39/00 | (2006.01) |
| C12N 7/00 | (2006.01) |
| C07K 14/005 | (2006.01) |
| A61K 39/12 | (2006.01) |
| A01N 63/00 | (2006.01) |
| C12N 15/86 | (2006.01) |

(52) U.S. Cl.
CPC .............. *C12N 7/00* (2013.01); *C07K 14/005* (2013.01); *C12N 15/86* (2013.01); *C12N 2740/13022* (2013.01); *C12N 2740/15043* (2013.01); *C12N 2740/15045* (2013.01); *C12N 2740/15051* (2013.01); *C12N 2740/15052* (2013.01); *C12N 2740/16021* (2013.01); *C12N 2740/16043* (2013.01); *C12N 2740/16051* (2013.01); *C12N 2760/20222* (2013.01)

(58) Field of Classification Search
CPC ....................... C12N 15/86; C12N 7/00; C12N 2740/15043; A61K 2300/00; C07K 14/005
See application file for complete search history.

(56) References Cited

U.S. PATENT DOCUMENTS

| | | | |
|---|---|---|---|
| 2014/0315294 A1 | 10/2014 | Marceau |
| 2017/0002332 A1 | 1/2017 | Boudeffa et al. |

FOREIGN PATENT DOCUMENTS

| | | | |
|---|---|---|---|
| WO | WO 2006/052813 | 5/2006 |
| WO | WO 2007/123961 | 11/2007 |
| WO | WO 2009/153563 | 12/2009 |
| WO | WO 2013/001041 | 1/2013 |
| WO | WO 2013/076309 | 5/2013 |
| WO | WO2013076309 | * 5/2013 |
| WO | WO 2015/092287 | 6/2015 |

OTHER PUBLICATIONS

Mctaggart et al., Biotechnology progress, American Institute of Chemical Engineers, US, 2000:859-865.*
Mc Taggart et al., Biotechnol., 2000, 16:859-865.*
Protocol: Lenti-Viral Transfection, 2010, XP055127370:1-2.*
Morizono et al., "Transient low pH treatment enhances infection of lentiviral vector pseudotypes with a targeting Sindbis envelope", 2006, 355:71-81.*
De Las Mercedes Segura, M. et al. "Downstream processing of oncoretroviral and lentiviral gene therapy vectors" *Biotechnology Advances*, May 2006, pp. 321-337, vol. 24, No. 3.
Herzer, S. et al. "Isoelectric titration curves of viral particles as an evaluation tool for ion exchange chromatography" *Life Science News*, 2003, pp. 16-18, vol. 13.
Rodrigues, T. et al. "Purification of retroviral vectors for clinical application: Biological implications and technological challenges" *Journal of Biotechnology*, Dec. 2006, pp. 520-541, vol. 127, No. 3.
Anonymous "Purification of influenza A/H1N1 using Capto™ Core 700" *GE Healthcare Life Sciences*, Mar. 2012, pp. 1-8, retrieved from the internet, URL:http://wolfson.huji.ac.il/purification/PDF/HCIC/GE_CaptoCore700PurificInfluenzaAH1.N1.pdf, XP055141530.
Written Opinion in International Application No. PCT/FR2014/053406, dated Mar. 17, 2015, pp. 1-8.
Higashikawa, F., et al., "Kinetic Analyses of Stability of Simple and Complex Retroviral Vectors," *Virology*, Feb. 2001, vol. 280, No. 1, pp. 124-131.
Holic, N., et al., "Influence of Mildly Acidic pH Conditions on the Production of Lentiviral and Retroviral Vectors," *Human Gene Therapy Clinical Development*, Sep. 1, 2014, vol. 25, No. 3, pp. 178-185.
McTaggart, S., et al., "Effects of Culture Parameters on the Production of Retroviral Vectors by a Human Packaging Cell Line," *Biotechnology Progress*, Sep. 2000, vol. 16, No. 5, pp. 859-865.
Morizono, K., et al., "Transient low pH treatment enhances infection of lentiviral vector pseudotypes with a targeting Sindbis envelope," *Virology*, Nov. 10, 2006, vol. 355, No. 1, pp. 71-81.
"Protocol: Lenti-Viral Transfection/Transduction," Nov. 2, 2010, XP055127370, pp. 1-2, retrieved from the Internet on Jul. 7, 2014: http://research.jax.org/faculty/mills/protocols/lentiviral_transfection.pdf.
Written Opinion in International Application No. PCT/FR2014/052279, dated Dec. 22, 2014, pp. 1-7.

(Continued)

*Primary Examiner* — Barry A Chestnut
(74) *Attorney, Agent, or Firm* — Saliwanchik, Lloyd & Eisenschenk

(57) ABSTRACT

The invention relates to a process for producing enveloped viruses in a mildly acid medium. The processes of the invention are useful for producing and recovering at a large scale enveloped viruses under conditions observing good manufacturing practice (GMP).

7 Claims, 6 Drawing Sheets

(56) References Cited

OTHER PUBLICATIONS

Williams, A.C., et al., "An acidic environment leads to p53 dependent induction of apoptosis in human adenoma and carcinoma cell lines: implications for clonal selection during colorectal carcinogenesis," *Oncogene*, 1998, vol. 18, pp. 3199-3204.

\* cited by examiner

METHOD FOR PRODUCING ENVELOPED VIRUSES

CROSS-REFERENCE TO RELATED APPLICATION

This application is the U.S. national stage application of International Patent Application No. PCT/FR2014/052279, filed Sep. 12, 2014.

The invention relates to a process for producing enveloped viruses produced by a cell culture in a mildly acid medium. The processes of the invention are useful for producing these particles for applications in biomedical or biotechnological research in order to facilitate the production yields notably when it is carried out on a large scale and under conditions observing good manufacturing practice (GMP).

TECHNOLOGICAL BACKGROUND

Enveloped viral vectors, and notably lentiviral vectors such as those derived from the human immunodeficiency virus-1 (HIV-1) are promising tools within the scope of gene therapy approaches. However, mass production of clinical grades of such vectors remains a challenge at the present time. Several approaches have been proposed for improving their production: optimization of the transfection of the plasmids required for producing the vector in the host cells (e.g., optimization of the transfection agent, of the cell density, of the ratio of plasmids, etc.) or cell culture conditions focused on particular cell metabolism routes (e.g., addition of lipids, cholesterol, chloroquine, sodium butyrate, etc.) (Ansorge et al. 2010; Schweizer and Merten 2010).

The inventors have the idea of extending this field and of optimizing physico-chemical parameters, and were more particularly interested in the pH conditions. The neutrality of the pH of the medium is considered as a critical parameter for cultivating mammal cells. Moreover, a study reported that pseudotyped lentiviruses with envelope glycoproteins of the virus of vesicular stomatitis (VSV-G) are unstable at pH 6 in a phosphate buffer (Higashikawa and Chang 2001). Considering these elements, the person skilled in the art would have considered that the reduction of pH in culture media would have a negative impact on the production of enveloped viruses.

SUMMARY OF THE INVENTION

The present invention results from the observation of improvement in the production of enveloped viruses when the cells producing said viruses are cultivated in a mildly acid medium. In a quite surprising way, said mildly acid conditions gave the possibility of producing viruses having infectious titers two to three times greater than those obtained in a conventionally used neutral medium.

Therefore the object of the invention is the use of mildly acid conditions for producing an enveloped virus. More particularly, the invention relates to a process for producing an enveloped lentiviral vector, characterized in that the culture medium used for cultivating the host cells producing said vector is a mildly acid medium.

DETAILED DESCRIPTION OF THE INVENTION

The invention therefore relates to a process for producing enveloped vectors characterized in that said vectors are produced under mildly acid conditions.

The expression "mildly acid condition" refers to the pH of an aqueous solution comprised between 5 and 6.6, in particular between 5.5 and 6.6 or between 5 and 6.2, more particularly between 5.8 and 6.2. The pH will notably be equal to 5.5, 5.6, 5.7, 5.8, 5.9, 6, 6.1 or 6.2. According to a particular embodiment, the pH is of about 6. The selected pH will also depend on the buffering power of the medium used, which the person skilled in the art will be able to easily determine considering his/her general knowledge.

The person skilled in the art is able to modify the pH of a solution, notably the pH of a cell culture medium. He/she may notably introduce into said solution a solution of an acid, notably of a strong acid such as hydrochloric acid. If need be, a solution of a base, notably of a strong base such as sodium hydroxide, may be used for readjusting the pH to bring it up to the desired value.

Except for mildly acid conditions which are the object of the present invention, the process used for producing enveloped viruses applies processes and materials well known in the field. The person skilled in the art may refer to his/her general knowledge in the production of enveloped viruses, notably illustrated by Ansorge et al. 2010; Schweizer and Merten 2010; and Rodrigues et al. 2011.

Within the scope of the present invention, the term of "virus" designates both a natural virus, as found in nature, and a modified virus, for which the genome includes modifications relative to that of the parent virus from which it is derived. This may be an attenuated virus, which has lost all or part of its pathogenic power as compared with the natural virus from which it is derived. Its genome is modified in vivo during successive passages in a cell culture or in a living organism. The term "virus" may also refer to a recombinant virus, for which the genome is modified in vitro by genetic engineering techniques. The modification may, for example, allow inactivation of at least one essential gene for viral replication (making the virus deficient for replication) and/or insertion of a DNA fragment coding for a protein or a heterologous RNA (normally not coded by the natural virus). In the latter case, this is referred to as a "viral vector". The insertion takes place in a suitable region of the viral genome, so as to allow expression of the heterologous DNA fragment in a target cell. The term "virus" also refers to pseudo-viral particles, i.e., viral particles either without any envelope glycoprotein at their surface, or without a genome and obtained by spontaneous assembling of structural and/or enzymatic proteins of the virus.

According to a particular embodiment, the enveloped virus is a viral vector. The viral vector is notably derived from a retrovirus, for example a lentivirus. The retroviral vectors produced according to the invention are notably derived from alpha-retroviruses (such as ALV for avian leukosis virus), from beta-retroviruses (such as MMTV for mouse mammary tumour virus), from gamma-retroviruses (such as the different types of MLVs for murine leukemia virus), from delta-retroviruses (such as the different types of HTLV for human T-lymphotropic virus), from epsilon-retroviruses (such as WDSV for Walleye dermal sarcoma virus), from spumaviruses (such as HFV for human foamy virus and SFV for simian foamy virus), from primate lentiviruses such as the different types of human immunodeficiency viruses (HIV for human immunodeficiency virus), the different types of simian immunodeficiency viruses (SIV for simian immunodeficiency virus), or from lentiviruses of non-primate mammals such as the virus of equine infectious anaemia (EIAV for equine infectious anaemia virus), the feline immunodeficiency virus (FIV for feline immunodeficiency virus), the virus of caprine arthritis-encephalitis (CAEV for caprine arthritis-encephalitis virus), or the ovine visna-maedi virus (VMV for visna maedi virus).

According to a particular embodiment, the retroviral vector in particular lentiviral vector is pseudotyped, i.e. it comprises an envelope glycoprotein derived from a virus different from the virus from which is derived the retroviral particle, a modified envelope glycoprotein or a chimeric envelope glycoprotein. According to a particular embodiment, the retroviral vector is pseudotyped with an envelope glycoprotein derived from the virus of vesicular stomatitis (VSV-G) or from the gibbon leukemia virus (GALV for gibbon ape leukaemia virus), although the person skilled in the art may contemplate the use of other viral envelope glycoproteins (Frecha et al. 2008). According to a particular embodiment, the retroviral vector, more particularly lentiviral vector, is pseudotyped with a modified envelope glycoprotein such as GALVTR (an envelope glycoprotein of GALV for which the intravirion C-terminal end has been replaced with the C-terminal end of the envelope glycoprotein of the amphotropic human leukaemogenic virus A-MLV, thus allowing highly efficient incorporation of the envelope glycoprotein into the lentiviral particle) (Christodoulopoulos and Cannon 2001). According to a particular embodiment, the retroviral vector, more particularly lentiviral vector, is pseudotyped with a chimeric envelope glycoprotein such as the envelope glycoprotein of the measles virus in which a fusion protein coding for the variable region of heavy and light chains of an immunoglobulin (scFv for single chain variable fragment) or a protein with repeated ankyrin domains (DARPins for designed ankyrin repeat proteins) have been inserted in order to allow specific targeting of a given receptor at the surface of the target cells (Anliker et al. 2010; Munch et al. 2011).

According to a particular embodiment, the viral envelope glycoprotein used for pseudotyping the retroviral vector, more particularly lentiviral vector, is derived from an envelope glycoprotein of a virus belonging to the family of rhabdoviridae, notably of the Vesiculovirus genus (e.g., VSV-G) or of the Lyssavirus genus (e.g., rabies virus, Mokola virus); to the family of Arenaviridae (e.g., lymphocyte choriomeningitis virus (LCMV)); to the family of togaviridae, more particularly of the alphavirus genus (e.g., Ross River Virus (RRV), Sindbis virus, Semliki Forest Virus (SFV), Venezuelan equine encephalitis virus, Western equine encephalitis virus); to the family of filoviridae, most particularly of the filovirus genus (e.g., Ebola virus, Lassa virus); to the family of retroviridae, more particularly of the alpharetrovirus genus (e.g., virus of avian leukosis (ALV), Rous Sarcoma Virus (RSV)), of the betaretrovirus genus (e.g., Jaagsiekte sheep retrovirus), of the gammaretrovirus genus (e.g., different murine leukaemia viruses (MLV), wild Baboon Ape Endogenous Virus (BAEV) or modified (BAEVTR), virus of Wild Gibbon Ape Leukaemia Virus (GALV) or modified (GALVTR)), of the deltaretrovirus genus (e.g., Human T-Lymphtrophic Virus (HTLV-1), of the spumavirus genus (e.g., human spumous virus), of the lentivirus genus (e.g., Maedi-Visna Virus (MMV)); to the family of coronaviridae, more particularly to the coronavirus genus (e.g., SaRS-CoV); to the family of paramyxoviridae, more particularly to the respirovirus genus (e.g., Sendai virus, human parainfluenza type 3 virus), of the henipavirus genus (e.g., Nipah virus), of the Morbillivirus genus (e.g., measles virus); to the family of flaviviridae, more particularly of the hepacivirus genus (e.g., hepatitis C virus (HCV)); to the family of orthomyxoviridae, more particularly of the influenza A virus genus (e.g., influenza virus); to the family of baculoviridae, more particularly of the nucleopolyhedrovirus genus (e.g., virus of Autographa californica multiple nuclear polyhedrosis). The envelope glycoprotein used for pseudotyping is more particularly a modified envelope glycoprotein, for example an envelope protein fused with an antibody fragment with a single variable chain ScFV, such as measles-ScFV, Tupaia-ScFV, Sindbis-ScFV envelope glycoprotein; an envelope protein fused with Ankirine repeat domains such as a measles/DARPins envelope protein; or further a VSV-G+nanobody display with defective binding protein.

According to a particular embodiment, the retrovirus, more particularly the lentivirus, produced according to the invention is pseudotyped with a VSV-G, measles, GALV or BAEV (if the virus is a retrovirus), GALVTR or BAEVTR (if the virus is a lentivirus) or baculovirus gp64 glycoprotein.

The enveloped virus may moreover contain a transgene of interest introduced into its genome. Of course, the transgene of interest will depend on the specific use for which the enveloped viral vector is intended. Illustratively, let us mention a transgene of interest coding for a therapeutic RNA (e.g., a transgene of interest coding for a complementary antisense RNA of a target RNA or DNA sequence), a gene therapy transgene coding for a deficient or absent protein in a subject affected with a pathology, or a transgene used for vaccination with DNA, i.e. a transgene coding for a protein, the expression of which will induce vaccination of the receiving organism against said protein. The process according to the invention therefore allows production of an enveloped viral vector which may be used in gene therapy. The process according to the invention is advantageously compatible with good laboratory practice and gives the possibility of contemplating large scale production of enveloped viral vectors, notably of lentiviral vectors, in particular pseudotyped lentiviral vectors (in particular with the VSV-G or GALVTR envelope proteins).

According to a preferred embodiment for producing a lentiviral vector, the four following elements are introduced into the host cell: an expression cassette comprising a lentiviral gagpol gene, an expression cassette comprising a lentiviral rev gene, an expression cassette of a transgene of interest comprised between a lentiviral LTR-5' and LTR-3', and an expression cassette of envelope glycoprotein(s).

In a particular embodiment, the enveloped virus, notably a retroviral vector, more particularly a lentiviral vector, is produced from a stable line expressing one or several elements required for producing an enveloped virus (Miller 2001; Rodrigues et al. 2011), such as the human productive line GPRG-EF1α-h$\chi_c$OPT which constitutively produces a lentiviral vector derived from HIV-1 pseudotyped with the VSV-G envelope glycoprotein (Greene et al. 2012), or for example the murine producing line PG13-MFG-GFP which constitutively produces the gamma-retroviral vector MLV pseudotyped with the GALV envelope glycoprotein (Merten 2004). In a particular embodiment, the enveloped virus is produced from a mammal host cell transiently transfected with one or several plasmids coding for the elements required for producing the virus. According to an alternative allowing production of a lentiviral vector, said elements are introduced into the cell by means of 4 plasmids: a plasmid bearing an expression cassette comprising a lentiviral gagpol gene, a plasmid bearing an expression cassette comprising a lentiviral rev gene, a transfer plasmid comprising an expression cassette of a transgene of interest comprised between a lentiviral LTR-5' and LTR-3' and a plasmid bearing an expression cassette of envelope glycoprotein(s).

The person skilled in the art will understand from the present disclosure that the cultivation in a mildly acid medium is carried out according to the invention as soon as the production of the virus is started, i.e., the producing cell is cultivated in a medium of which the pH is mildly acid before contact with the producing cells. According to a particular embodiment, the cell is cultivated in a mildly acid medium 5 to 24 hours after transfection, more particularly 10 to 20 hours post-transfection, even more particularly 16 to 20 hours post-transfection.

The host cell may be selected from any cell allowing production of an enveloped virus. According to a particular embodiment, said cell is selected from a human cell (HEK293, HEK293T, HEK293FT, Te671, HT1080, CEM), a muridae cell (NIH-3T3), a mustelid cell (Mpf), a canid cell (D17) (Miller 2001; Miller and Chen 1996; Merten 2004; Rodrigues et al. 2011; Stacey and Merten, 2011).

The cells are cultivated in a suitable medium for cultivating mammal cells and for producing an enveloped virus. The medium may moreover be supplemented with additives well known in the field such as antibiotics, serum (notably fetal calf serum, etc.) added in suitable concentrations. The medium used may notably comprise serum or be without any serum. The media for cultivating mammal cells are well known in the field. Mention may be made as such of the DMEM (Dulbecco's Modified Eagle's medium), RPMI1640 or a mixture of different culture media, for example DMEM/F12, or a medium without any serum like optiMEM®, optiPRO®, optiPRO-SFM®, CD293®, Freestyle F17® (Life Technologies) or Ex-Cell® 293 (Sigma-Aldrich).

In the processes using transiently transfected cells, any agent allowing transfection of plasmids may be used. Notably the use of calcium phosphate or polyethylenimine may notably be made, although other agents may be contemplated by the person skilled in the art (Ansorge et al. 2010). The conditions (notably amount of plasmid(s), ratio between the plasmids, ratio between the plasmid(s) and the transfection agent, the type of medium, etc.) and the transfection period may be adapted by the person skilled in the art according to the characteristics of the produced virus and/or of the transgene introduced into the transfer plasmid.

The enveloped virus is then harvested from the culture supernatant according to methods well known in the field.

According to a particular embodiment, the process according to the invention comprises the following steps:
transiently transfecting HEK293T cells by means of one or several plasmids coding for the elements required for producing said enveloped vector;
cultivating said cells in a suitable medium, of which the pH is of about 6; and
harvesting the enveloped virus in the culture supernatant.

According to an alternative of this embodiment, the produced enveloped virus is a lentivirus produced after transfection of the cells by means of four plasmids: one plasmid bearing an expression cassette comprising a lentiviral gagpol gene, one plasmid bearing an expression cassette comprising a lentiviral rev gene, one transfer plasmid comprising an expression cassette of a transgene of interest comprised between a lentiviral LTR-5' and LTR-3' and one plasmid bearing an expression cassette of envelope glycoprotein(s). According to an alternative, the envelope protein is derived from the VSV virus (in particular VSV-G envelope) or from the GALV virus (in particular the GALVTR modified glycoprotein for lentiviral vectors).

The viruses or viral vectors produced may then be purified according to processes well known to the person skilled in the art (Segura et al. 2011).

The invention moreover relates to a medium for cultivating mammal cells, said medium being mildly acid. In particular, the culture medium is at a pH comprised between 5.5 and 6.6, more particularly between 5.8 and 6.2. More particularly, the pH of the culture medium according to the present invention is of about 6. According to another particular embodiment, the culture medium is mildly acid DMEM, notably with a pH as defined hereinbefore. In particular, the culture medium according to the invention is a DMEM medium with a pH comprised between 5.8 and 6.2, in particular a DMEM medium of pH 6. It is understood that the culture medium according to the invention is characterized by a mildly acid pH before cultivating the cells.

The invention moreover relates to a kit for applying the process for producing enveloped viruses as defined above, comprising a mildly acid culture medium, or a culture medium accompanied by one or several useful solutions for bring the pH of said medium to a mildly acid value, the kit further comprising:
(a) one or several suitable plasmids for producing the enveloped virus; and/or
(b) suitable cells for producing said virus.

The kit of the invention is intended for producing an enveloped virus according to the invention. Thus, it may further comprise instructions for use of the different constituents of the kit allowing production of an enveloped virus according to the invention. In particular, these instructions may indicate how the cells intended for the production have to be transfected with the suitable plasmids and cultivated in the culture medium. In particular, the instructions indicate that the cells producing the enveloped virus have to be cultivated in a culture medium with a mildly acid pH as detailed above.

The invention also relates to a kit for applying the process for producing enveloped viruses as defined above, comprising (i) means for applying said process and (ii) instructions to be followed for applying the process. According to a particular embodiment, the means comprised in the kit are selected from among one or several of the following means:
(a) one or several suitable plasmids for producing the enveloped virus;
(b) suitable cells for producing said virus; and
(c) a mildly acid culture medium, or a culture medium accompanied by one or several solutions useful for bringing the pH of said medium to a mildly acid value.

A kit according to the invention may thus notably comprise the means (a) and (b), (a) and (c), (b) and (c) or (a) and (b) and (c).

The invention also relates to a kit for applying the process for producing enveloped viruses as detailed above, comprising a culture medium accompanied by one or several useful solutions for bringing the pH of said medium to a mildly acid value.

EXAMPLES

Equipment and Methods
Cell Culture

HCT116 cells derived from a human colorectal carcinoma (CCL-247; ATCC, Manassas, Va.), HEK293T cells of a human embryo kidney (Merten et al. 2011), and cells producing gamma-retrovirus GALV-MLV (PG13-MFG-GFP line) (Fenard et al. 2013) were cultivated at 37° C., with 5% $CO_2$ in Dulbecco's modified Eagle's medium (DMEM+Glutamax) supplemented with 2 to 10% of fetal calf serum (FCS) inactivated by heat (Life Technologies, St-Aubin, France). The DMEM/FCS medium was buffered to the indicated pH values by using hydrochloric acid or sodium hydroxide, and was then sterilized on a filter (0.220.

Production of Viral Vectors and Titration

The lentiviral vectors derived from HIV-1 were generated by transient transfection with calcium phosphate of 4 plasmids in HEK293T cells (Fenard et al. 2013): the expression plasmids of gagpol (pKLgagpol) and of rev (pBArev), the transfer plasmid coding for the green fluorescent protein GFP (pCCL-eGFP) and the plasmid coding for the GALVTR envelope glycoprotein (pBA.GALV/Ampho-Kana) or VSV-G (pMDG). At 16 to 20 hrs after transfection, the HEK293T cells were washed and incubated in the DMEM/SVF medium buffered to the indicated pH value, comprised between 6 and 8. After 24 h of production, the viral supernatants were collected, filtered (0.450 and frozen at −80° C. The titers of physical particles were determined by quantitative measurement of the p24 capsid of the HIV-1 by means of a commercial ELISA kit (PerkinElmer, Courtaboeuf, France). The infectious titers were determined on HCT116 cells by detecting the GFP by flow cytometry (FACSCalibur, BD Biosciences, Le Pont de Claix, France), the titers being expressed in transduction units per milliliter (TU/ml) (Fenard et al. 2013).

Exposure of the Viral Vectors to a Temperature of 37° C. and to Multiple Freezing/Thawing Cycles Tubes for freezing of 1 ml containing GALVTR-LV supernatant (lentiviral vector pseudotyped with the envelope glycoprotein GALVTR) produced at pH 7.2 or 6 were incubated for the indicated time at 37° C. (the tubes with screw caps remaining closed). Next, the tubes were again frozen at −80° C. and titrations on HCT116 cells were carried out simultaneously for all the conditions in order to prevent inter-experiment variations.

For the stability experiments to freezing/thawing, the first and second freezing/thawing cycles were carried out in parallel with two different samples from the same production of GALVTR-LV. This procedure allows the simultaneous evaluation of all the infectious titers of GALVTR-LV in order to avoid any inter-experiment variability.

Western Blot and Analysis

Figure 1:
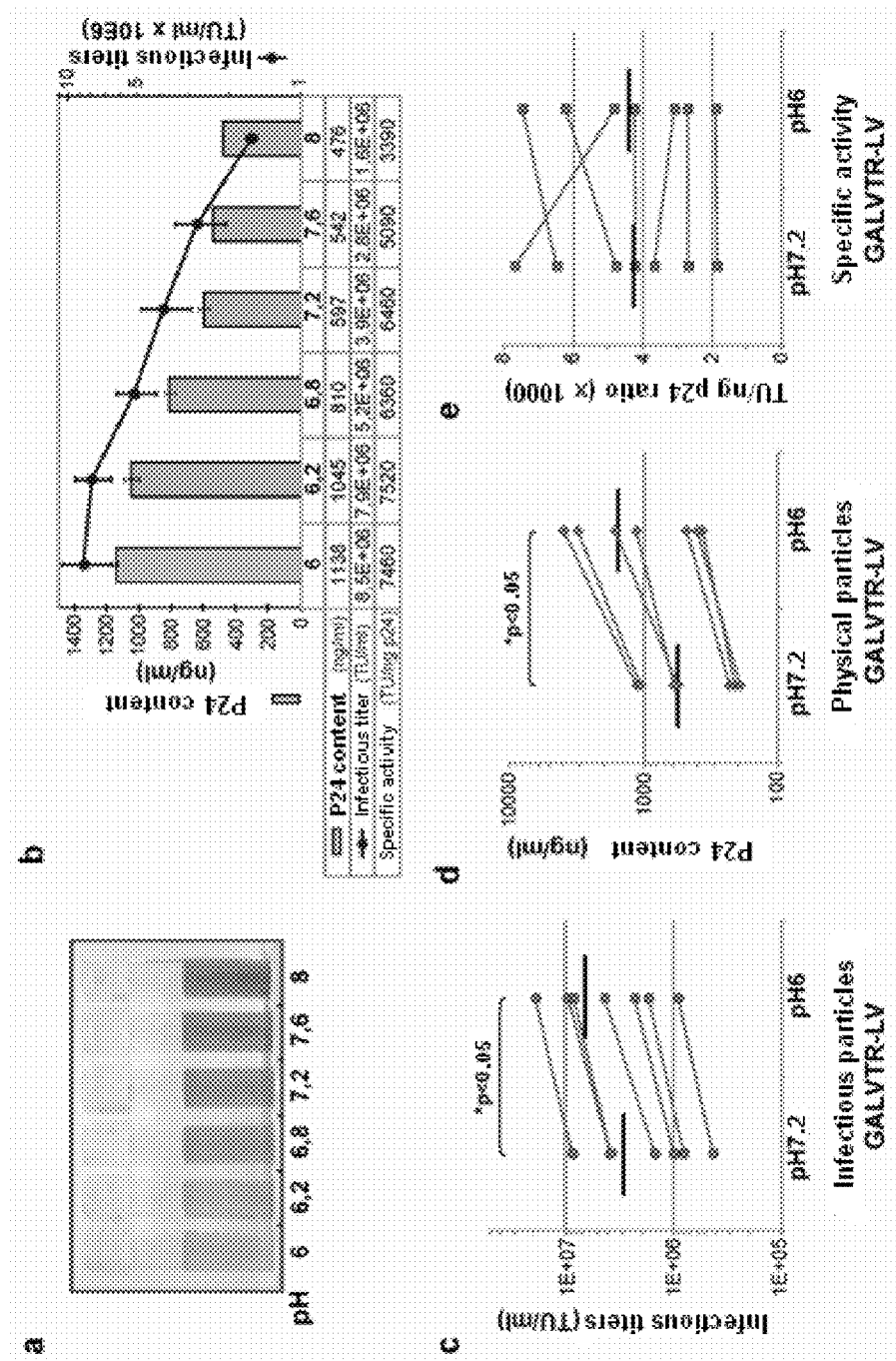
FIG. 1. Production of a lentiviral vector (LV) pseudotyped with the GALVTR envelope (GALVTR-LV) under diverse pH conditions. (a) The culture media (DMEM/FCS) were buffered to the indicated pH with hydrochloric acid or sodium hydroxide. The pH indicator contained in the medium (phenol red) has a color ranging from yellow (pH 6) to violet (pH 8). (b) GALVTR-LV particles were produced from HEK293T cells cultivated in a DMEM/SVF medium at the indicated pH value. The infectious titers (TU/ml) were determined after transduction of HCT116 cells and quantification of the expression level of the GFP transgene by flow cytometry. The contents of the supernatants of physical particles GALVTR-LV were quantified by quantitative measurement of the capsid p24 of HIV-1 by means of a commercial ELISA kit. The specific activity corresponding to the ratio between the infectious titers and the amount of physical particles (TU/ng of p24) is illustrated under the histograms. The results represent the average of two independent experiments±the standard deviation. Seven batches of GALVTR-LV vector were produced in the medium at pH 7.2 or pH 6 and were titrated for their contents of infectious particles (c) or of physical particles (d). (e) The specific activity of each GALVTR-LV supernatant is illustrated. The bars indicate the average value of the distributions.
Figure 2:
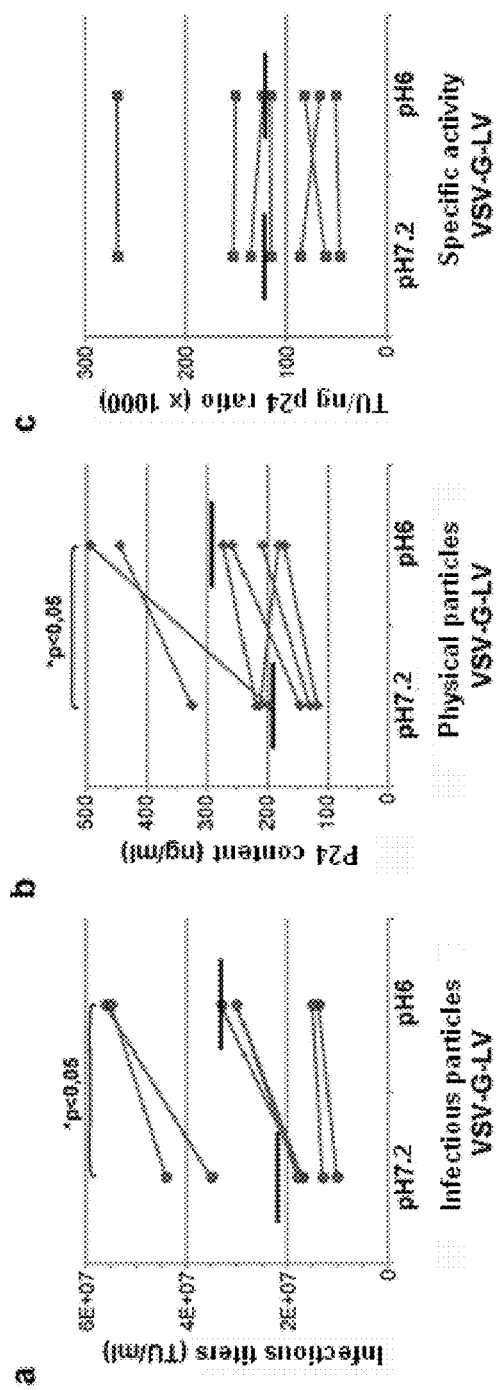
FIG. 2. Production of a VSV-G-LV lentiviral vector under neutral or slightly acid pH conditions. (a) Six VSV-G-LV vector batches were produced from HEK293T cells cultivated in DMEM/SVF medium at the indicated pH. The infectious titers were determined as in FIG. 1b. (b) The amount of physical particles was determined by quantitative measurement of the p24 capsid of the HIV-1 by means of a commercial ELISA kit. (c) The specific activity of each VSV-G-LV supernatant is illustrated. The bars indicate the average value of the distributions.
Figure 3:
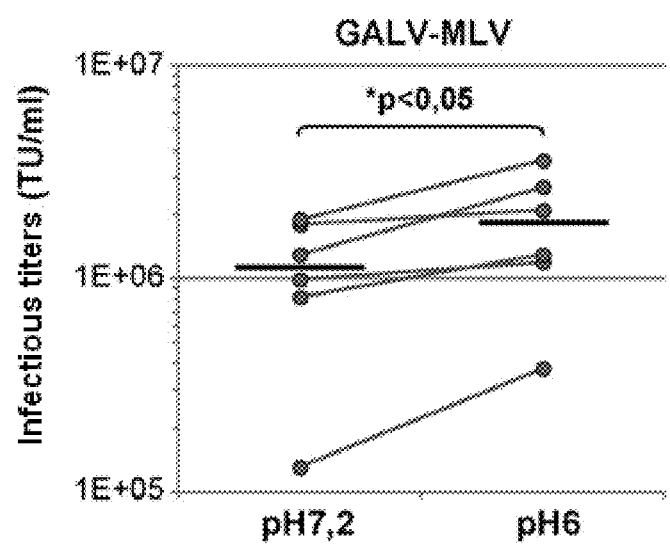
FIG. 3. Production of a GALV-MLV gamma-retroviral vector under neutral or slightly acid pH conditions. Six GALV-MLV vector batches were produced from HEK293T cells cultivated in DMEM/SVF medium at the indicated pH. The infectious titers were determined as in FIG. 1b. The bars indicate the average value of the distributions.

The producing cells were washed and lyzed in a buffer containing 50 mM of Tris-HCl pH 7.5, 200 mM of NaCl, 1% of Triton X-100, 0.1% of SDS, 0.5% of sodium deoxycholate, 10% of glycerol, 1 mM of EDTA, and 1 mM of PMSF supplemented with a cocktail of protease inhibitors (complete protease inhibitor cocktail, Roche Diagnostics, Meylan, France). The protein concentrations were determined by means of the Bio-Rad DC Protein Assay kit I (Bio-Rad, Marnes-la-Coquette, France). The proteins (30 μg/track) were separated on 10% SDS-polyacrylamide electrophoresis gel (PAGE) and transferred on a nitrocellulose membrane Hybond ECL (GE Healthcare Life Sciences, Velizy-Villacoublay, France) and an immunoblot was produced by combining a goat anti-p24 antibody (AbD Serotec, Oxford, UK) and a mouse anti-actin antibody (AC-15 clone) (Sigma-Aldrich, St-Quentin-Fallavier, France). An anti-goat donkey antibody coupled with IRDye 800 and an anti-mouse donkey antibody coupled with IRDye 680 were used as secondary antibodies (Eurobio, Courtaboeuf, France). The immunoreactive bands were detected with the infrared Odyssey scanner and quantified with the analysis software Odyssey 3.0 (LI-COR Biosciences, Lincoln, Nebr.).
Statistical Analyses The values P were determined with the non-parametric Wilcoxon test by means of the GraphPad Prism 5 software.
Results
Production of a GALVTR-LV Lentiviral Vector in a Mildly Acid Culture Medium The lentiviral vectors (LV) pseudotyped by means of the GALVTR envelope glycoprotein (GALVTR-LV) transduct in a highly effective way the hematopoietic stem cells (Sandrin et al. 2002; Jacome et al. 2009). However, the large scale production of this type of vectors remains a major challenge. The production efficiency of GALVTR-LV vectors in various culture mediums of pH 6 to 8 was evaluated (FIG. 1a). FIG. 1b shows that the infectious titers obtained at pH 8 are strongly reduced relative to those at the typical pH of 7.2. On the contrary, and in a quite surprising way, the infectious titers of GALVTR-LV produced in a medium at pH 6 are significantly greater (2.3×) to those obtained at pH 7.2 (FIGS. 1b and 1c). It is important to note that we observed in parallel an increase in the amount of p24 antigen in the GALVTR-LV supernatants produced at pH 6 (FIGS. 1b and 1d). This positive correlation leads to a stable specific activity between the vectors produced at neutral or mildly acid pH (FIGS. 1b and 1e), while this specific activity is strongly reduced at pH 8 (FIG. 1b). The use of mildly acid conditions therefore represents the optimum condition for producing large amounts of GALVTR-LV vector.
Effect of the Mildly Acid pH Conditions on the Production of Lentiviral Vectors Pseudotyped with the VSV-G Protein and on MLV Gamma-Retroviral Vectors Pseudotyped with the GALV Protein The encouraging results obtained with the GALVTR-LV vector urged us to test these same conditions for producing a lentiviral vector pseudotyped with an envelope glycoprotein very widely used in the field: the VSV-G protein (VSV-G-LV vectors). FIG. 3 shows that a medium at pH 6 allows significant increase in the production of infectious VSV-G-LV particles (FIG. 2a) and of physical VSV-G-LV particles (FIG. 2b), on average by a factor of 1.5, with stable specific activity (FIG. 2c). The deleterious effects of a pH equal to 6 reported by the Higashikawa team (op. cit.) are probably a consequence of the procedure used by these authors, who produced retroviral particles at a neutral pH, concentrated them and then diluted them in a non-ionic solution buffered to pH 6, causing a loss of infectivity of the viral supernatant by 90%. Unexpectedly, the VSV-G-LV particles, directly produced in a culture medium at pH 6 supplemented with FCS, are not only stable but also, unexpectedly produced at a higher level when they are produced from a culture medium at pH 7.2, conventionally recognized as optimal for this type of production.

Figure 4:
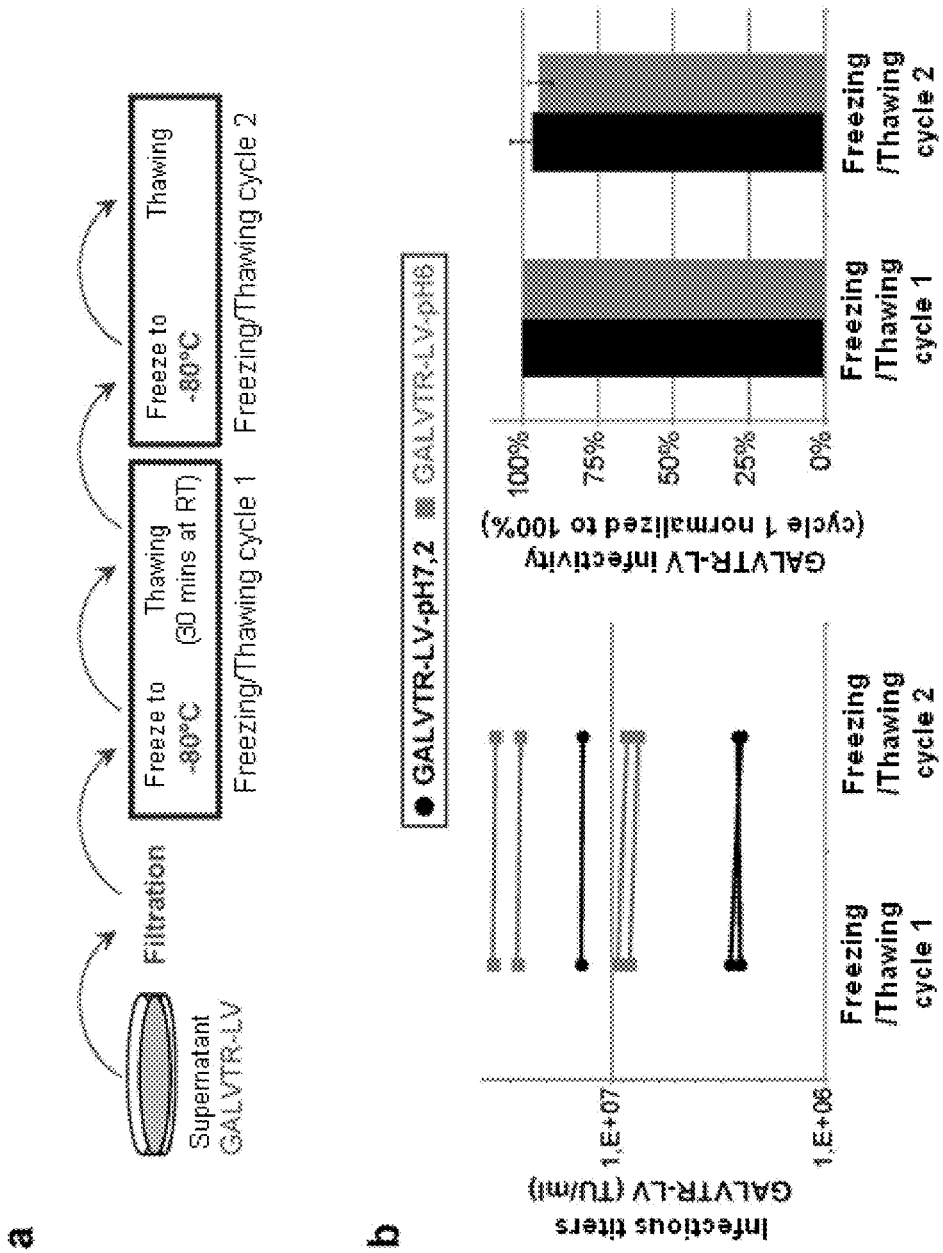
FIG. 4. Study of the stability of GALVTR-LV lentiviral particles after several freezing/thawing cycles. (a) Schematic illustration of the freezing/thawing procedure for the vectors. (b) Several GALVTR-LV vector batches, produced at pH 7.2 (black) or pH 6 (grey), were exposed to one or two freezing/thawing cycles. The infectious titers were determined as in FIG. 1b. The data represent the various infectious titers obtained (left figure) or were normalized to 100% relative to the condition corresponding to one freezing/thawing cycle (right figure). Room Temperature (R.T.), Freezing (Freez.), Thawing (Thaw.).

In order to ensure that the observed improvement does not depend on the HEK293T cells used, or upon producing the sole lentiviral vectors, the effect of the mildly acid pH was evaluated on the cell line PG13-MFG-GFP, producing GALV-MLV (MLV gamma-retrovirus pseudotyped with the envelope glycoprotein GALV) (Merten 2004). The original PG13 cell line is a cell line of murine fibroblasts (NIH-3T3) transfected in a stable way with a packaging system of the MLV virus (pLGPS) and a construct coding for the GALV envelope glycoprotein (pMOV-GALV) (Miller et al. 1991). In order to produce in a constitutive way the retroviral GALV-MLV pseudotypes, the transfer plasmid coding for the GFP protein placed under control of the LTR promoter of MLV (pMFG-GFP) was introduced in a stable way into the PG13 line. In cell cultures produced in parallel, the PG13-MFG-GFP cells were incubated in DMEM buffered to pH 7.2 or pH 6 and 24 to 48 hours later, the contents of infectious particles in the harvested supernatants were evaluated. FIG. 3 shows that the production of GALV-MLV particles is significantly increased at a mildly acid pH. This result is particularly interesting since it shows that the proposed production process is not limited to a human cell line such as the HEK293T line, and that in addition to being particularly adapted for the production of lentiviral vectors, it is not limited to the production of vectors of the lentivirus genus since other enveloped viruses may be produced more efficiently by means of the procedure of the invention.
Stability of the GALVTR-LV Particles Exposed to Several Freezing/Thawing Cycles The harvested supernatants of lentiviral vectors are generally stored at −80° C. before purification. It might have been assumed that the mildly acid pH conditions would have the deleterious effect of increasing the inactivation of the virions during the freezing or thawing procedure. The supernatants of GALVTR-LV particles were therefore subjected to one or two freezing/thawing cycles, the infectious titers having been determined at each thawing step (FIG. 4a). FIG. 4b shows that the mildly acid conditions do not affect the infectivity of the particles. The average reduction in infectious titers after two freezing/thawing cycles as compared with a single cycle is only of 5% both at pH 7.2 and pH 6. The infectivity is therefore not altered when the lentiviral vectors are frozen under mildly acid conditions.
Effect of Long Term Exposure of the GALVTR-LV Particles to a Temperature of 37° C.

Figure 5:
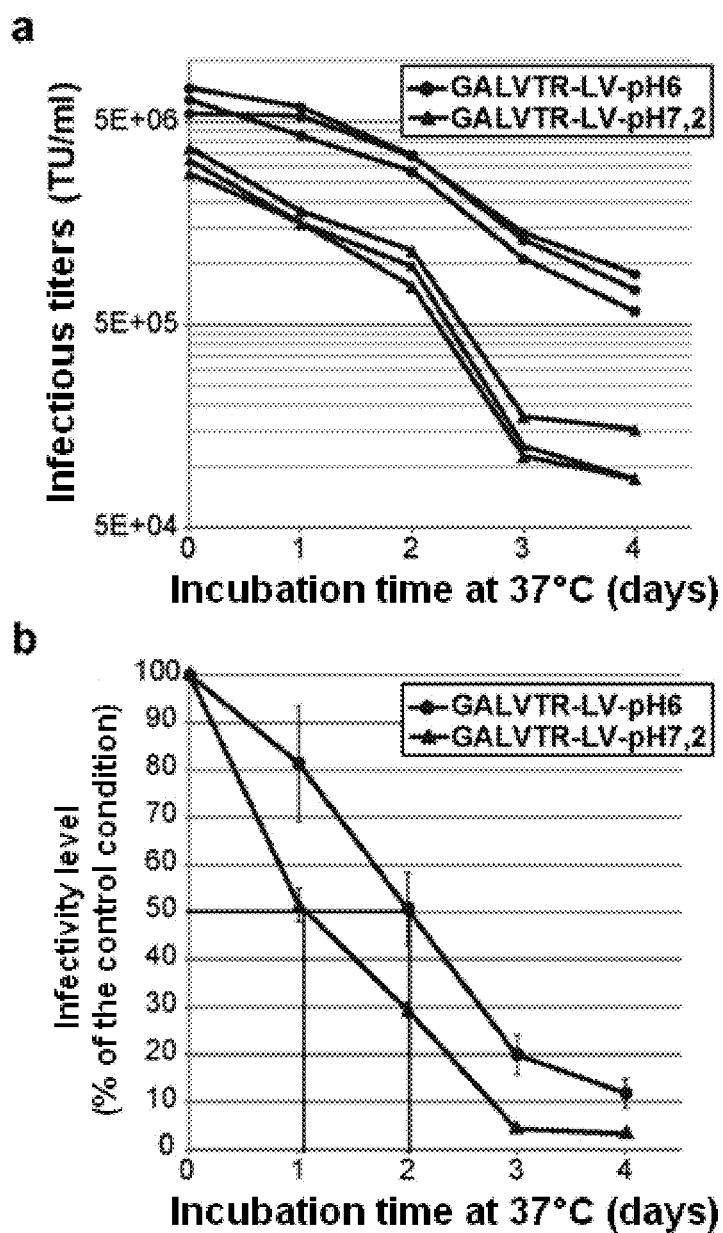
FIG. 5. Study of the stability of GALVTR-LV lentiviral particles after exposure to a temperature of 37° C. The cryotubes containing one milliliter of GALVTR-LV particles, produced at pH 7.2 or pH 6, were incubated at 37° C. for 0 to 4 days. Next, the infectious titers were determined as in FIG. 1b. (a) The data are represented either as the infectious titers obtained from three independent experiments or (b) the average of the infectious titers±the standard deviation and normalized to 100% relative to the control condition (a condition corresponding to a GALVTR-LV vector not exposed at 37° C.).

During lentiviral transduction, the target cells, which in our case are mammal cells, are cultivated at a temperature of 37° C. We therefore sought to determine whether the production of lentiviral vectors at a mild acid pH had a deleterious effect on their stability after a more or less long exposure to a temperature of 37° C. For this, the tubes for freezing containing supernatant of GALVTR-LV vectors produced at pH 7.2 or pH 6 were incubated for 0 to 4 days at 37° C. and the infectivity decreased kinetics were tracked. As shown in FIG. 5a, whereas the infectious titers, after a long exposure to 37° C., are strongly reduced, both for the GALVTR-LV vectors produced at pH 7.2 and for the vectors produced at pH 6, the slope of this decrease is less pronounced for GALVTR-LV vectors produced at pH 6. The resulting half-life of the GALVTR-LV vectors produced at pH 6 is double that observed for the GALVTR-LV vectors produced at pH 7 (around 2 days versus one day; see FIG. 5b). Interestingly, this experiment showed that the crude supernatants of GALVTR-LV vectors are rather resistant (half-life from one to 2 days) at a temperature of 37° C. in a closed environment (tube with closed screwed-on cap). This is to be opposed with the stability in a cell culture showing a half-life of only 6 h (Strang et al. 2004), which suggests that parameters other than the temperature, such as oxidative stress, also have to be taken into consideration when the stability of the lentiviral vectors is evaluated in a cell culture at 37° C.
Modulation of the Intracellular Expression Level of p55gag in HEK293T Producing Cells Cultivated at a Mildly Acid pH.

Figure 6:
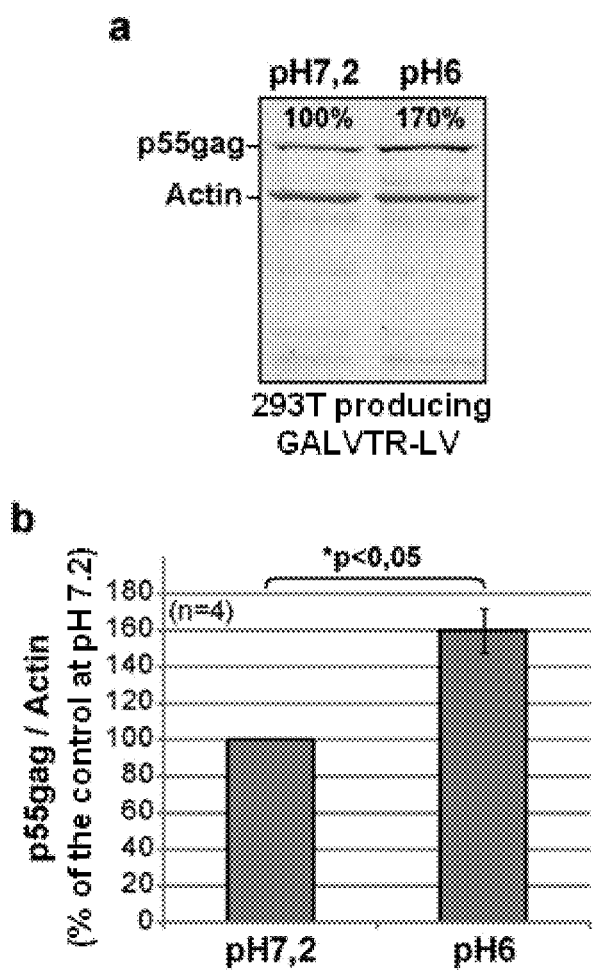
FIG. 6. Study of the expression levels of intracellular p55gag in producing HEK293T cells cultivated in a medium at neutral or slightly acid pH. (a) Western blot of the expression of p55gag in lyzates of HEK293T cells producing the GALVTR-LV vector at pH 7.2 or pH 6. The expression level of p55gag is normalized relative to the expression level of the actin. (b) The histograms represent the average expression level of p55gag normalized relative to the expression level of the actin in four independent experiments±the standard deviation.

The amount of p24 proteins of HIV-1 harvested in the supernatants GALVTR-LV is improved under mildly acid conditions (FIGS. 1b and 1d). We therefore sought to determine whether this increase might be the consequence of an increase in the intracellular expression level of the p55gag precursor protein of HIV-1 in the producing cells. In FIG. 6a, an immunoblotting experiment shows an increase in the intracellular expression of p55gag at pH 6 relative to pH 7.2, with an average overexpression of 160% (FIG. 6b). This positive correlation between the intracellular overexpression of p55gag and the increase in the amounts of p24 protein in lentiviral supernatants suggests that mildly acid conditions generate an environment which is more favorable to optimal expression of the viral components.

BIBLIOGRAPHIC REFERENCES

Anliker, B., T. Abel, S. Kneissl, J. Hlavaty, A. Caputi, J. Brynza, et al. (2010). "Specific gene transfer to neurons, endothelial cells and hematopoietic progenitors with lentiviral vectors." Nat. Methods 7(11): 929-935.
Ansorge, S., O. Henry and A. Kamen (2010). "Recent progress in lentiviral vector mass production." Biochem. Eng. J. 48(3): 362-377.
Christodoulopoulos, I. and P. M. Cannon (2001). "Sequences in the cytoplasmic tail of the gibbon ape leukemia virus envelope protein that prevent its incorporation into lentivirus vectors." J. Virol. 75(9): 4129-4138.
Fenard, D., D. Ingrao, A. Seye, J. Buisset, S. Genries, S. Martin, et al. (2013). "Vectofusin-1, a new viral entry enhancer, strongly promotes lentiviral transduction of human hematopoietic stem cells." Mol Ther Nucleic Acids 2: e90.
Frecha, C., J. Szecsi, F. L. Cosset and E. Verhoeyen (2008). "Strategies for targeting lentiviral vectors." Curr. Gene Ther. 8(6): 449-460.
Greene, M. R., T. Lockey, P. K. Mehta, Y. S. Kim, P. W. Eldridge, J. T. Gray, et al. (2012). "Transduction of human CD34+repopulating cells with a self-inactivating lentiviral vector for SCID-X1 produced at clinical scale by a stable cell line." Hum Gene Ther Methods 23(5): 297-308.
Higashikawa, F. and L. Chang (2001). "Kinetic analyses of stability of simple and complex retroviral vectors." Virology 280(1): 124-131.
Jacome, A., S. Navarro, P. Rio, R. M. Yanez, A. Gonzalez-Murillo, M. L. Lozano, et al. (2009). "Lentiviral-mediated genetic correction of hematopoietic and mesenchymal progenitor cells from Fanconi anemia patients." Mol. Ther. 17(6): 1083-1092.
Merten, O. W. (2004). "State-of-the-art of the production of retroviral vectors." J. Gene Med. 6 Suppl 1: S105-124.
Merten, O. W., S. Charrier, N. Laroudie, S. Fauchille, C. Dugue, C. Jenny, et al. (2011). "Large-scale manufacture and characterization of a lentiviral vector produced for clinical ex vivo gene therapy application." Hum. Gene Ther. 22(3): 343-356.
Miller, A. D. (2001). "Production of retroviral vectors." Curr. Protoc. Hum. Genet. Chapter 12: Unit 12 15.
Miller, A. D., J. V. Garcia, N. von Suhr, C. M. Lynch, C. Wilson and M. V. Eiden (1991). "Construction and properties of retrovirus packaging cells based on gibbon ape leukemia virus." J Virol 65(5): 2220-2224.
Miller A D, Chen F. (1996). "Retrovirus packaging cells based on 10A1 murine leukemia virus for production of vectors that use multiple receptors for cell entry." J. Virol. 70: 5564-5571.
Munch, R. C., M. D. Muhlebach, T. Schaser, S. Kneissl, C. Jost, A. Pluckthun, et al. (2011). "DARPins: an efficient targeting domain for lentiviral vectors." Mol. Ther. 19(4): 686-693.
Rodrigues, A. F., P. M. Alves and A. S. Coroadinha (2011). "Production of Retroviral and Lentiviral Gene Therapy Vectors: Challenges in the Manufacturing of Lipid Enveloped Virus." Viral Gene Therapy. K. Xu, InTech. Chapter 2: 15-40.
Sandrin, V., B. Boson, P. Salmon, W. Gay, D. Negre, R. Le Grand, et al. (2002). "Lentiviral vectors pseudotyped with a modified RD114 envelope glycoprotein show increased stability in sera and augmented transduction of primary lymphocytes and CD34+ cells derived from human and non-human primates." Blood 100(3): 823-832.
Schweizer, M. and O. W. Merten (2010). "Large-scale production means for the manufacturing of lentiviral vectors." Curr. Gene Ther. 10(6): 474-486.
Segura, M. M., A. A. Kamen and A. Garnier (2011). "Overview of current scalable methods for purification of viral vectors." Methods Mol Biol 737: 89-116.
Stacey G N, Merten O-W (2011) Chapter 3: "Hosts cells and cell banking." In: Merten O-W, Al-Rubeai M (eds.): Viral Vectors for Gene Therapy: Methods and Protocols, in the series of: Methods in Molecular Biology 737, Humana Press, New York, N.Y., pp 45-88.
Strang, B. L., Y. Ikeda, F. L. Cosset, M. K. Collins and Y. Takeuchi (2004). "Characterization of HIV-1 vectors with gammaretrovirus envelope glycoproteins produced from stable packaging cells." Gene Ther. 11(7): 591-598.

The invention claimed is:

1. A process for producing an enveloped virus comprising cultivating host cells producing said enveloped virus in a mildly acidic culture medium, wherein the enveloped virus is a lentivirus, optionally pseudotyped.

2. The process according to claim 1, the mildly acidic medium having a pH between 5.8 and 6.2.

3. The process according to claim 1, the lentivirus being pseudotyped with an envelope protein selected from the VSV-G envelope protein or the GALVTR envelope protein.

4. The process according to claim 1, the host cell being a HEK293, HEK293T, HEK293FT, Te671, CEM, NIH-3T3, Mpf, or D17 cell.

5. The process according to claim 1, said process comprising the following steps:
 transient transfection of HEK293T cells by means of one or several plasmids coding for the elements required for producing said enveloped vector;
 cultivation of said cells in a suitable medium, of which the pH is about 6; and
 harvesting the enveloped virus in the culture supernatant.

6. The process according to claim 5, the cells being transfected by means of four plasmids: one plasmid bearing an expression cassette comprising a lentiviral gagpol gene, one plasmid bearing an expression cassette comprising a lentiviral rev gene, one transfer plasmid comprising an expression cassette of a transgene of interest, comprised between a lentiviral LTR-5' and a LTR-3', and one plasmid bearing an expression cassette of envelope glycoprotein(s).

7. The process according to claim 1, wherein said cells are cultivated in a mildly acid medium 5 to 24 hours after transfection.

* * * * *

UNITED STATES PATENT AND TRADEMARK OFFICE
CERTIFICATE OF CORRECTION

PATENT NO. : 10,125,352 B2
APPLICATION NO. : 15/022049
DATED : November 13, 2018
INVENTOR(S) : David Fenard Page 1 of 1

It is certified that error appears in the above-identified patent and that said Letters Patent is hereby corrected as shown below:

In the Specification

<u>Column 8,</u>
Line 22, "(0.450 and" should read --(0.45µ) and--.

Signed and Sealed this
Seventeenth Day of September, 2019

Andrei Iancu
*Director of the United States Patent and Trademark Office*